US00PP17549P3

(12) United States Plant Patent
Brouwer et al.

(10) Patent No.: US PP17,549 P3
(45) Date of Patent: Apr. 3, 2007

(54) APPLE TREE NAMED 'SJ303'

(50) Latin Name: *Malus domestica*
Varietal Denomination: SJ303

(75) Inventors: Jan W. Brouwer, Eaton (AU); Richard T. Atherton, Eaton (AU); Catherine S. Portman, Eaton (AU)

(73) Assignee: Skyglow Enterprises Pty Ltd, Boyanuf (AU)

( * ) Notice: Subject to any disclaimer, the term of this patent is extended or adjusted under 35 U.S.C. 154(b) by 0 days.

(21) Appl. No.: 11/158,321

(22) Filed: Jun. 21, 2005

(65) Prior Publication Data

US 2006/0037116 P1 Feb. 16, 2006

Related U.S. Application Data

(60) Provisional application No. 60/585,120, filed on Jul. 2, 2004.

(51) Int. Cl.
*A01H 5/00* (2006.01)

(52) U.S. Cl. ..... Plt./172

(58) Field of Classification Search ..... Plt./172, Plt./161
See application file for complete search history.

*Primary Examiner*—Kent Bell
(74) *Attorney, Agent, or Firm*—Stratton Ballew PLLC

(57) ABSTRACT

A new apple tree (*Malus domestica*) named 'SJ303' is disclosed. The fruit of 'SJ303' is notable for its exceptional taste, appearance, and storageability.

3 Drawing Sheets

Latin name: *Malus domestica.*
Variety denomination: 'SJ303'.

BRIEF DESCRIPTION OF THE PHOTOGRAPHS

BRIEF DESCRIPTION OF THE VARIETY

Figure 1:
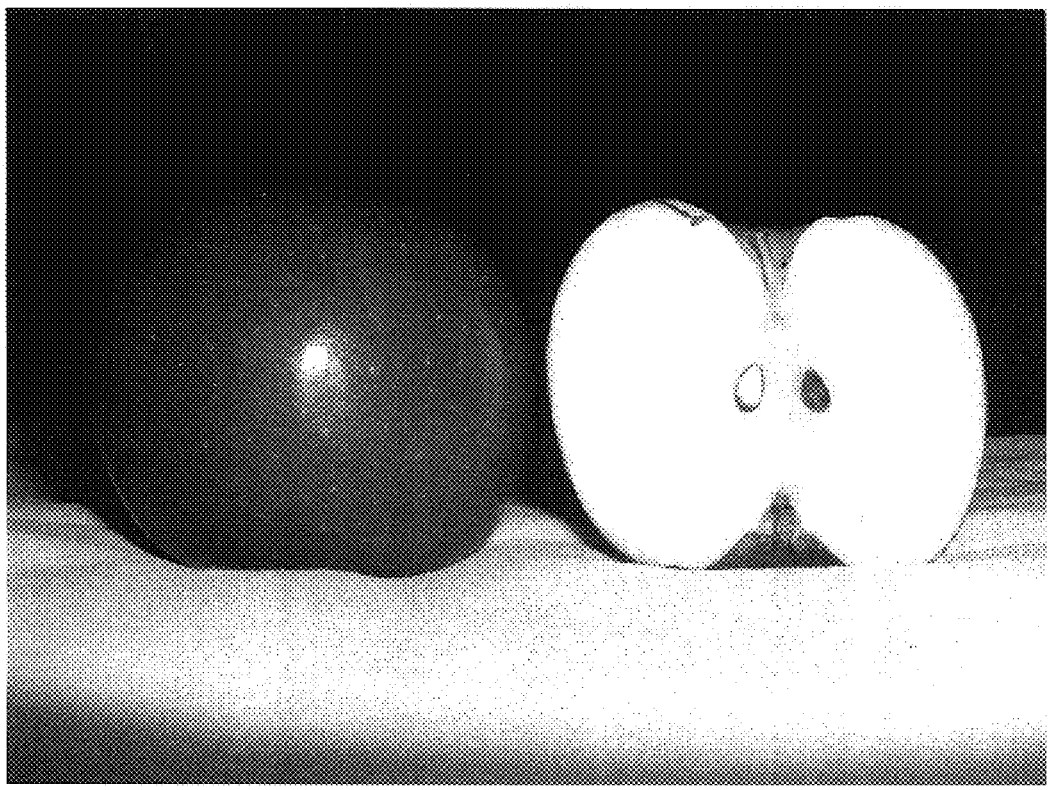
FIG. 1 illustrates the fruit of 'SJ303' in cross-section.
Figure 2:
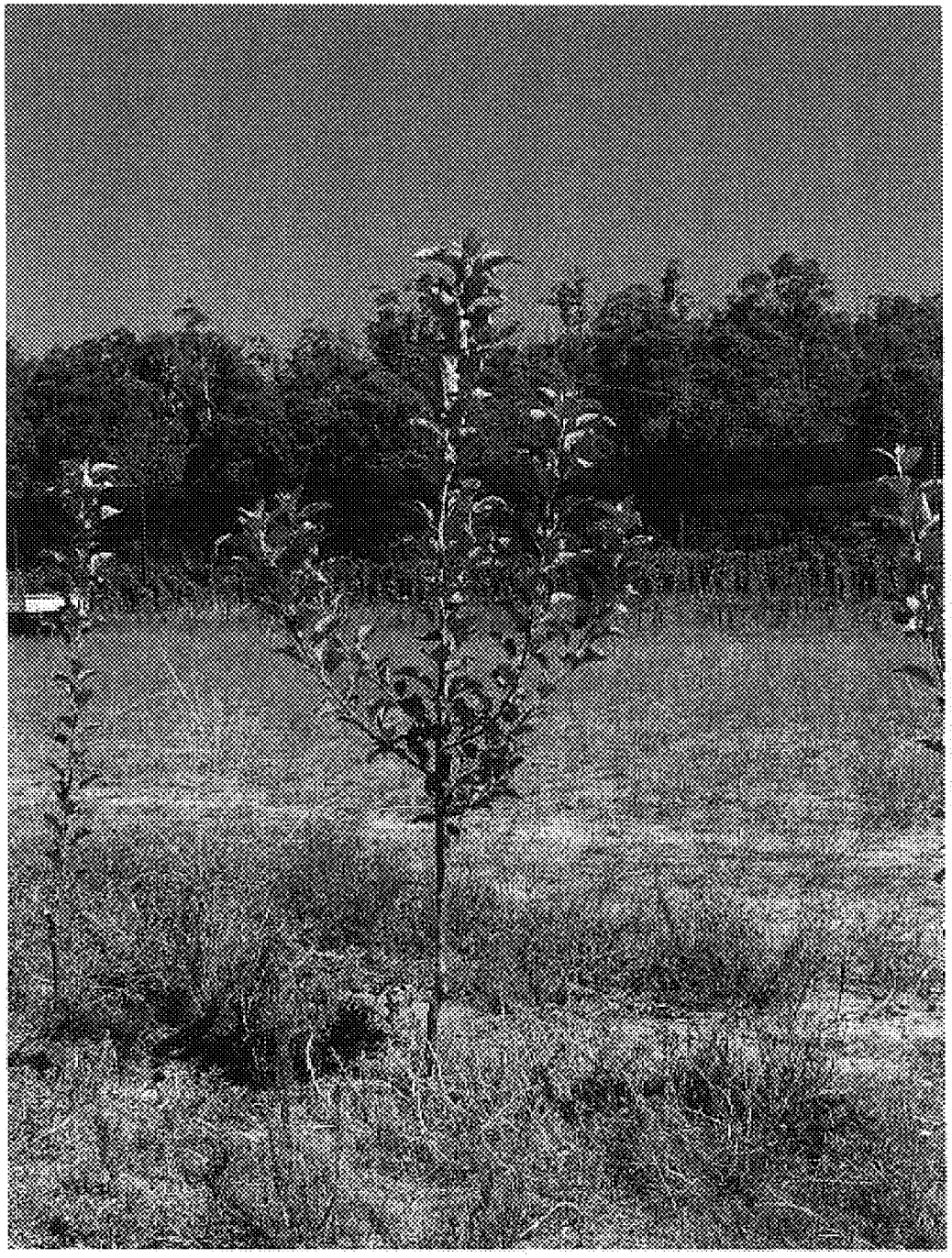
FIG. 2 illustrates a one-year-old 'SJ303' tree in the nursery, grafted on MM109 rootstock, indicating shape of tree and branch angles.
Figure 3:
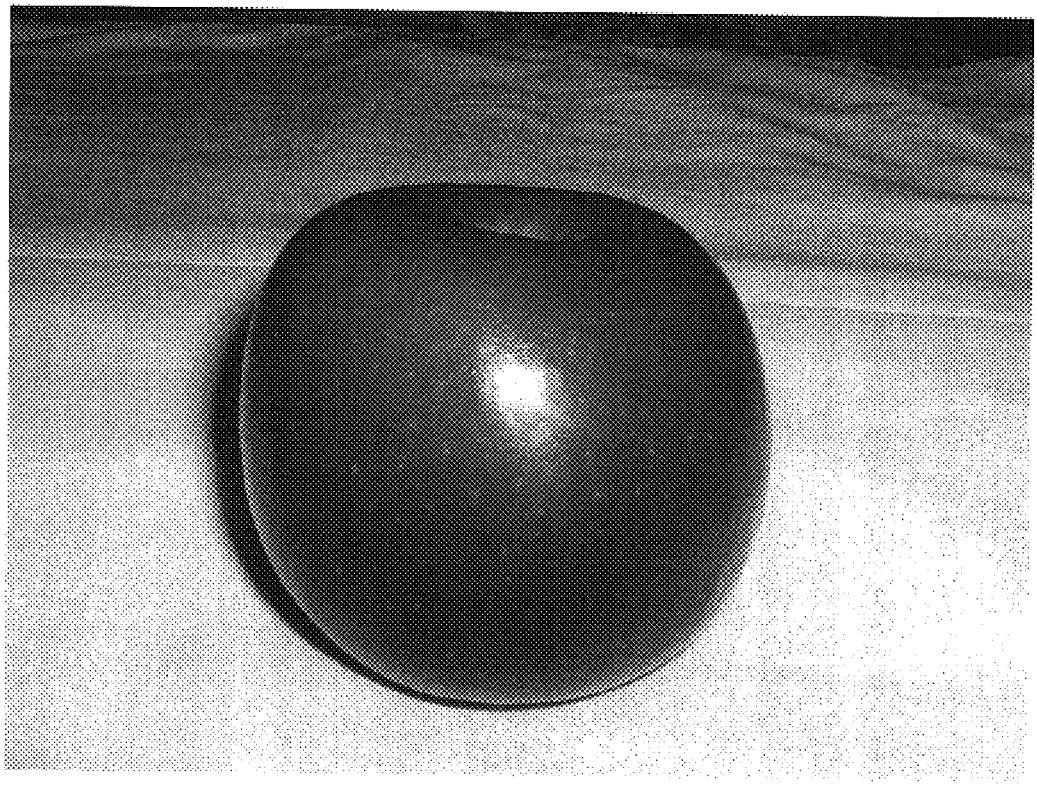
FIG. 3 illustrates the fruit of 'SJ303.'

The present invention relates to a new and distinct variety of apple tree named 'SJ303' that was discovered as a chance seedling, which germinated in some home-made compost and was subsequently grown on in a pot. The probable parents are 'Lady Williams' and 'Granny Smith', two varieties grown and consumed on the property where 'SJ303' was discovered. The fruit coloration and storageability traits of 'SJ303' are similar to those of 'Lady Williams'. Reasons for selection of this seedling for further propagation were that the fruit showed exceptional qualities of taste, appearance, and storageability.

The seedling was first discovered in Thompsons Brook, Western Australia in 1998. The first asexual propagation (grafting) of the variety took place in July 2003 in Boyanup, Western Australia. 'SJ303' has been observed to remain true to type over successive asexually propagated generations.

DETAILED BOTANICAL DESCRIPTION OF THE VARIETY

The following detailed description is based on information gathered from the originally identified seedling (six years old) and from one-year-old-asexually produced progeny growing on 'MM109' rootstocks in Boyanup, Western Australia. Size descriptions are given as an average of five to twenty samples taken from different trees. Color descriptions refer to The Royal Horticultural Society Colour Chart. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

1. Tree:
   - *Vigor.*—Strong.
   - *Type.*—Ramified.
   - *Habit.*—Upright/Spreading.
   - *Size.*—Height, 1.97 m; diameter, 0.84 m.
   - *Trunk.*—Diameter 1.95 cm at 50 cm above graft union; bark texture smooth; color grey/orange RHS 168B.
   - *Branches* (*original seedling*).—Branches start to emerge at 0.8 m above ground level, then at intervals of 0.5, 0.2, 0.15, 0.17 m evenly arranged around trunk. Length 95 cm; diameter 1.5 cm; crotch angle 50 to 90 degrees; color Grey-orange 165A.
   - *Winter hardiness.*—Not known.
   - *Chilling requirement.*—Estimated at 450 hour (units below 7.2 degrees centigrade).
2. Dormant one year old shoot:
   - *Pubescence.*—Medium.
   - *Size.*—Diameter 5 mm; length 77 cm.
   - *Color.*—Grey-orange RHS 165A.
   - *Internode length.*—1.89 cm.
   - *Number of lenticels.*—Medium.
3. Flowers:
   - *Bud.*—One per spur; shape oval; length 1.25 cm; diameter 0.18 cm; color grey-purple 183A.
   - *Flower color* (*balloon stage*).—Red-purple 58A.
   - *Size.*—Small; diameter 25 mm; depth 12 mm; Quantity per Cluster 5–6.

*Petals.*—Five per flower; overlapping; length 1.4 cm; width 0.9 cm; shape rounded to ovate with pointed tip; margins smooth; upper surface color white 155D; lower surface color red-purple 62D when fully open.

*Sepal.*—Five per flower; shape conical, long, pointed; length 5.5 mm; color light green 142D.

*Pedicel length.*—9 mm; diameter 1.65 mm; color pale green 145C.

*Pistil.*—Length 7 mm; color pale brown 162D.

*Anthers.*—18 per flower; length 1.7 mm; pollen color pale cream yellow 12C.

*Stigma.*—Size 0.3 mm; color green 146D.

*Style.*—Length 3.8 mm; color yellow-green 150C.

*Ovary.*—Size 2.4 mm; color green 143D.

*Bloom period.*—First bloom Oct. 17, 2004 at Boyanup, Western Australia. Dates may change due to amount of cold units per season.

4. Leaf:

*Attitude in relation to shoot.*—Outward.

5. Leaf blade:

*Length.*—9.2 cm.

*Width.*—6.1 cm.

*Length-width ratio.*—1.5.

*Margin.*—Serrate.

*Shape.*—Broadly acute.

*Color.*—Upper surface yellow-green 148A; lower surface yellow-green 147B.

6. Petiole: Length 28 mm; diameter 2.5 mm; color greyed-purple 185B.

7. Fruit:

*Maturity and harvest dates.*—Medium; last week of March, first week of April in 2002.

*Size.*—Mass 185 g average; diameter 75.3 mm; height 64 mm.

*Ratio of height to width.*—1.18.

*General shape in profile.*—Round.

*Position of maximum diameter.*—Central.

*Ribbing.*—None.

*Crowning at calyx end.*—Absent or very weak.

*Aperture of eye.*—0.8 cm.

*Size of eye.*—Medium.

*Depth of eye basin.*—1.3 cm.

*Width of eye basin.*—3.2 cm.

*Stalk.*—Diameter 2 mm; length 12 mm; color yellow-green 152D.

*Depth of stalk cavity.*—1.4 cm.

*Width of stalk cavity.*—1.6 cm at outer edge.

*Size of lenticels.*—Small.

*Bloom of skin.*—Absent or very weak, glossy when polished.

*Greasiness of skin.*—Absent or very weak.

*Ground color of skin.*—Green-yellow 153D.

*Over color of skin.*—Red 46B.

*Amount of over color.*—High>70% Average.

*Intensity of over color.*—Medium.

*Pattern of over color.*—Solid flush with slight striping of darker red.

*Flesh.*—Texture medium firmness; juiciness moderate; Color white 155A.

*Seeds.*—5–8 per fruit; acute shape; length 7.5 mm; width 4.8 mm; color greyed-orange 175B.

*Quantity per cluster.*—5 fruits per cluster.

*Aroma.*—Moderate.

*Resistance to known diseases.*—Not known.

*Storageability, keeping quality.*—Fruit remains fresh at room temperature for 25 days after 6 months in cold air storage at 0.degrees centigrade.

*Yield.*—Average yield 43 kilos per tree on Malling Merton 106 rootstock.

We claim:

1. A new and distinct apple tree substantially as illustrated and described herein.

* * * * *